United States Patent [19]

Kaufman

[11] 4,370,344

[45] * Jan. 25, 1983

[54] 5'-AMINOALKYL-4'-ALKYLPSORALENS

[75] Inventor: Kurt D. Kaufman, Kalamazoo, Mich., by Marilee Kaufman, conservator

[73] Assignee: Elder Pharmaceuticals, Inc., Hamilton, Ind.

[*] Notice: The portion of the term of this patent subsequent to Nov. 3, 1998, has been disclaimed.

[21] Appl. No.: 236,644

[22] Filed: Feb. 23, 1981

Related U.S. Application Data

[63] Continuation-in-part of Ser. No. 73,908, Sep. 10, 1979, Pat. No. 4,298,614.

[51] Int. Cl.$^3$ .................. C07D 493/04; A61K 31/34
[52] U.S. Cl. .................................. 424/279; 549/282; 548/463

[58] Field of Search .................. 260/343.21; 424/279, 424/59

[56] References Cited

U.S. PATENT DOCUMENTS

| | | | |
|---|---|---|---|
| 4,124,598 | 11/1978 | Hearst et al. | 260/343.21 |
| 4,130,568 | 12/1978 | Confalone et al. | 260/343.21 |
| 4,269,851 | 5/1981 | Kaufman | 260/343.21 |

Primary Examiner—Jane T. Fan
Attorney, Agent, or Firm—Gordon W. Hueschen

[57] ABSTRACT

The invention relates to 5'-aminoalkyl-4'-alkylpsoralens, having essentially no erythematic photosensitizing activity but at the same time having substantial DNA-binding photosensitizing activity, making them of especial interest from the standpoint of suntanning and psoriasis treatment, characteristics which are unpredictable when the compounds are compared with psoralens of similar but different structure.

6 Claims, No Drawings

5'-AMINOALKYL-4'-ALKYLPSORALENS

This application is a continuation-in-part of my prior-filed copending application Ser. No. 073,908, filed Sept. 10, 1979, now U.S. Pat. No. 4,298,614, issued Nov. 3, 1981.

BACKGROUND OF THE INVENTION

1. Field of the Invention

Chemical compounds, photochemotherapy, compounds having an enhanced combination of photosensitizing properties for use in photochemotherapy, selective photosensitizing agents.

2. Prior Art

Psoralens have been used for years as dermal photosensitizing agents, e.g., in the treatment of vitiligo. Their topical and/or oral application, followed by irradiation with light, results in stimulation of melanin, thus producing a tanning effect. They have accordingly also been used for such cosmetic purpose. More recently, psoralens have been found useful in the photochemotherapeutic treatment of psoriasis, in which case they are administered orally or topically to the subject, whose skin is subsequently exposed to controlled ultraviolet radiation, as in Psoralite (TM) apparatus. A high percentage of emissions of this disease have been effected in such manner.

The effectiveness of a psoralen for such uses and for such purpose has in the past related to its ability to produce erythema upon the skin upon irradiation. Psoralens also have other uses, and their uses, as well as underlying rationale and theory, are partially elucidated in U.S. Pat. Nos. 4,124,598 and 4,130,568, and are otherwise well-known in the art from various preexisting publications.

Rather recently, it has been found that the erythema, produced upon the skin of a patient or animal upon irradiation with ultraviolet light "A" in a so-called PUVA evaluation or application, after administration of psoralen to the subject, is associated with the linear structure of psoralens. This makes it possible for psoralens to engage in photocycloaddition reactions with double bonds of pyrimidine bases of macromolecules, such as present in the complementary strands of DNA (deoxyribonucleic acid), in a manner such that two double bonds of the psoralen compound react so as to produce two (2) cycloadditions with two (2) separate molecules of the pyrimidine base, as present in the complementary strands of DNA, thereby forming an interstrand crosslinkage. Such interstrand crosslinkages occur in photoreactions between highly erythematic linear psoralens and DNA. On the other hand, some psoralens, because of their angular structure, can engage, for geometric reasons, only one of the two photoreactive sites, thus effecting a single cycloaddition to only one of the two complementary strands of DNA with consequent production of a monofunctional adducts. In other words, psoralen compounds in the photoreaction with DNA can form either or both of monofunctional and bifunctional adducts, and this capacity varies with the type of psoralen compound involved, some compounds forming essentially only monofunctional adducts, whereas other compounds form solely or a preponderance of bifunctional adducts or interstrand crosslinkages. The ability or capacity to form only monofunctional and not bifunctional adducts, or at least minimization of bifunctional cycloaddition or bifunctional adduct formation, is now considered desirable from the standpoint that the consequences deriving from bifunctional damage are considered to be more serious from a biological repair standpoint than the consequences deriving from monofunctional cycloaddition or adduct effects. This means that it is at least no longer considered necessary that a compound exhibit strong bifunctional effects, as evidenced by a high degree of erythema in usual test procedures, for it to be useful in photochemotherapy, but that it is even preferred for it to produce monofunctional adducts or a single cycloaddition without interstrand crosslinkage to DNA. Psoralen compounds which produce monofunctional adducts only, or at least in preponderance, have been found effective in the treatment of psoriasis and in producing other desirable effects, such as tanning, even though they do not cause interstrand crosslinkages and consequent erythema. Such unique properties therefore constitute desirable and much sought after criteria or desideratum in the evaluation of photosensitizing compounds but, as already stated, up until the present time such psoralen compounds as produce monofunctional DNA adducts have been angular in their nature, such as some isopsoralens (or angelicins). However, the compounds of the present invention, despite their linear structure, for unknown reasons, are characterized by inability to crosslink DNA molecules and cause erythema, while nevertheless possessing ability to cause DNA monoaddition and production of monofunctional adducts, a totally unpredictable combination of characteristics for linear psoralen compounds. Further, linear psoralens are also characterized by established and recognized reactivity with ribonucleic acids (RNA), and accordingly the new psoralen compounds find use in the study of secondary structures of nucleic acids, as inhibitors of RNA replication, and in the inactivation of viruses, as well as in the photochemotherapy of psoriasis and in suntanning, all important uses.

The standard tests and test procedures, and their significance, are fully elucidated in the following publications: F. Dall'Acqua, S. Marciani, G. Rodighiero: Interstrand crosslinkages occurring in the photoreaction between psoralen and DNA. FEBS letters 9, 121 (1970); F. Dall'Acqua, S. Marciani, L. Ciavatta, G. Rodighiero: Formation of interstrand cross-linkings in the photoreactions between furocoumarins and DNA. Zeitschrift Naturforsch. 26b, 561 (1971); Baccichetti et al., Z. Naturforsch. 34c, 811–814 (1979); Bordin et al., Biochimica et Biophysica Acta 447, 249–259 (1976); Baccichetti et al., Experientia 35, 183 (1979); and see U.S. Pat. Nos. 4,124,598 and 4,130,568, as well as Hearst et al., Nucleic Acids Res. 1977, 4(5), 1339–1347; Isaacs et al., Biochemistry 1977, 16(6), 1058–1064; Shen et al., J. Mol. Biol. 1977, 116(4), 661–679; and Johnson et al., Science 1977, 197(4306), 906–908.

The unique linear psoralen compounds of the present invention then, which possess the characteristic, when employed in PUVA therapy, of forming only monofunctional adducts or essentially so, without concurrent interstrand DNA crosslinkages or erythema, thus finding employment and use in the foregoing manners, particularly in the photochemotherapy of tanning and psoriasis, should be welcome additions to the physicians' armamentarium of useful drugs.

OBJECTS OF THE INVENTION

It is an object of the invention to provide novel psoralen compounds. It is a further object to provide novel psoralen compounds of unique structure which have a beneficial or enhanced combination of characteristics when compared with psoralen compounds of similar but different structure. It is an additional object to provide novel psoralen compounds having beneficial or enhanced photosensitizing characteristics in accord with the foregoing stated criteria. It is a still further object to provide novel psoralen compounds having beneficial or enhanced photosensitizing characteristics, relatively low toxicity, and of a structure differing essentially from known psoralen compounds, the beneficial combination of properties of which could not be predicted on a basis of known structure-activity relationships. Still other objects will be apparent to one skilled in the art and still additional objects will become apparent hereinafter from the following description and claims.

SUMMARY OF THE INVENTION

The present invention relates to 5'-aminoalkyl-4'-alkylpsoralens having beneficial or enhanced photosensitizing activity, especially oral activity, as well as low toxicity, when compared with psoralens of similar but different structure. It is particularly concerned with 5'-primaryaminoloweralkyl-4'-loweralkylpsoralens, and especially 5'-aminomethyl-4'-methylpsoralen and salts thereof. It is to be noted that the compounds of this invention have no eight (8) carbon atom methyl or methoxy substituent as in the prior art compounds trisoralen (4,5',8-trimethylpsoralen), 8-methoxypsoralen, or the compounds of U.S. Pat. Nos. 4,124,598 or 4,130,568. Despite this fact, and the fact that they are characterized by essential absence of DNA crosslinking and/or erythematic photosensitization activity, they are characterized by DNA-binding (monocyloaddition or monofunctional adduct production) which approaches that of 8-methoxypsoralen, a widely-recognized and commonly-employed photosensitizing agent. These new compounds are therefore characterized by surprising and unpredictable selective photosensitization activity, i.e., DNA-binding activity without concurrent erythematic activity, according to the aforesaid criteria, as well as a relatively low toxicity.

The compounds of the invention have the formula

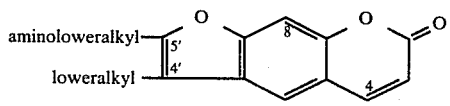

5'-primaryaminoloweralkyl-4'-loweralkylpsoralen, wherein loweralkyl is preferably methyl.

DETAILED DESCRIPTION OF THE INVENTION

The following Preparations and Examples are given by way of illustration only and are not to be construed as limiting.

The appropriate starting 7-hydroxycoumarin is a well-known compound which can be prepared in known manner and converted to psoralens by known procedure (MacLeod and Worth, Tetrahedron Lett., 237–240(1972)). Variations in the alkylhalomethyl ketone reactant produces variations in the alkyl group at position 4' of the resulting psoralen as will appear more fully hereinafter, especially from the Examples which follow. Chloroalkylation with a selected chloroalkyl methyl ether introduces a desired chloroalkyl group into the 5' position of the 4'-alkylpsoralen nucleus, whereafter reaction with potassium phthalimide followed by cleavage with hydrazine acetate yields the desired 5'-aminoalkyl-4'-alkylpsoralen, in which the various alkyl groups correspond to those in the reactants employed in converting the starting 7-hydroxycoumarin, namely, the alkylhalomethyl-ketone (4' position) and the chloroalkylating agent (5' position) employed. Alternatively, the haloalkylation may be effected according to Olah and Kuhn, J. Org. Chem. 29, 2317 (1964) or Friedel-Crafts and Related Reactions, Vol. II, Part 2, G. A. Olah, ed., Interscience, New York, New York, 1964, page 749. The structure of the final 5'-aminoalkyl-4'-alkylpsoralen is confirmed by nuclear magnetic resonance spectra, using a Perkin-Elmer Model R-24B.

Thin layer chromatography (TLC) was performed on Silica Gel $GF_{254}$ glass-backed slides, 250 microns thick, manufactured by Analtech, Inc. The eluent was benzene:2-butanone::17:3 unless otherwise indicated. NMR spectra were run on Perkin-Elmer Model R-24B. Melting points were taken on either a Fisher Digital Melting Point Analyzer, Model 355, or on a Thomas Hoover Capillary Melting Point Apparatus. All melting points are uncorrected.

5'-AMINOMETHYL-4'-METHYLPSORALEN

7-Acetonyloxycoumarin.

A mixture of potassium iodide (1.0 g, 6 mmol), chloroacetone (28.43 mL, 33.03 g, 0.357 mole) and reagent grade acetone (400 mL., dried over $K_2CO_3$) was allowed to stand overnight. 7-Hydroxycoumarin (50.0 g, 0.308 mol), anhyd. $K_2CO_3$ (49.34 g, 0.357 mole), and dry reagent grade acetone (1 L) were added and the mixture was refluxed for about 24 hours with overhead stirring and protection from atmospheric moisture (Drierite-TM tube). The hot reaction mixture was filtered and the precipitate was washed with two portions (200 mL) of dry reagent grade acetone. The filtrate and washes were combined and evaporated in vacuo to obtain a first crop. A mixture of the precipitate and water (1 L) was extracted with two portions (700 mL) of trichloromethane, which were combined, dried ($MgSO_4$), and evaporated in vacuo to obtain more product. A trichloromethane ($CHCl_3$) solution (3 L) of the two crops was washed once with 5% aqueous NaOH (1 L), and then three times with water (1 L), dried ($MgSO_4$), and evaporated, in vacuo to obtain crude 7-acetonyloxycoumarin (64.65 g, 96%), mp 168.2°–169.9° C., which was suitable for use in the next step. Recrystallization of a portion from 95% ethanol gave a purer sample (85.3% recovery, 82% yield), mp 174.6°–174.8° C. (previous run: mp 166.9°–167.1° C.) The NMR ($CDCl_3$) spectrum was identical to that obtained in the previous run.

4'-Methylpsoralen.

A stirred (overhead) mixture of 7-acetonyloxycoumarin (crude, 61.92 g, 0.284 mole) and 0.1 N aqueous potassium hydroxide (3.3 L) was heated under gentle reflux for six hours, allowed to cool to room temperature, and acidified with 1.0 N hydrochloric acid (about 500 mL). A yellow precipitate was collected by filtration, washed with water until free of acid, and placed in $CHCl_3$ (3 L). After removal of a brown, $NaHCO_3$-soluble solid, the $CHCl_3$ solution was washed with two portions (2 L) of saturated aqueous $NaHCO_3$, once with water (2 L), and dried ($MgSO_4$). Evaporation in vacuo yielded crude 4'-methylpsoralen (36.09 g, 63.5%), mp 187.4°–189.1° C. Recrystallization gave a purer product (78% recovery, 50% yield), mp 194.3°–195.2° C. (previous run: 187.1°–187.7° C.). NMR (CDCl$_3$) δ2.25 (d, 3, J≅1 Hz, 4'-CH$_3$), 6.26 (d, 1, J=9 Hz, C$_3$H), 7.27 (s, 1, C$_8$H), 7.36 (d, 1, J≅1 Hz, C$_5$, H), 7.47 (s, 1, C$_5$H), 7.70 (d, 1, J=9 Hz, C$_4$H).

5'-Chloromethyl-4'-methylpsoralen.

Chloromethyl methyl ether (75 mL, 988 mmol) was added to a solution of 4'-methylpsoralen (8.612 g, 43 mmol) in glacial acetic acid (600 mL) and the solution was stirred at room temperature for 24 hours. Another portion (75 mL) of chloromethyl methyl ether was added and stirring was allowed to continue for another forty hours, although crystallization began to occur after a total reaction time of about forty hours. Water (3.75 L) was added and a cream-colored precipitate was collected by suction filtration, washed with water, and dried in vacuo to obtain 5'-chloromethyl-4'-methylpsoralen (7.60 g, 71%), mp 181.7°–182.9° C. An analytical sample of colorless needles, mp 183.9°–184.8° C., was obtained from a further run by filtering the reaction mixture before diluting it with water. NMR (CDCl$_3$) δ2.3 (s, 3, 4'-CH$_3$), 4.7 (s, 2, CH$_2$Cl), 6.35 (d, 1, J=9 Hz, C$_3$H), 7.35 (s, 1, C$_8$H), 7.50 (s, 1, C$_5$H), 7.75 (d, 1, J=9 Hz, C$_4$H).

Anal. Calcd. for C$_{13}$H$_9$O$_3$Cl: C, 62.79; H, 3.65; Cl, 14.26. Found: C, 63.07; H, 3.72; Cl, 14.23.

4'-Methyl-5'-phthalimidomethylpsoralen.

A mixture of 5'-chloromethyl-4'-methylpsoralen (7.618 g, 30.6 mmol), potassium phthalimide (6.80 g, 36 mmol), and dimethylformamide (500 mL) was stirred and heated at 100° C. for six hours. It was concentrated in vacuo to a cream-colored paste, diluted with water (400 mL), and filtered, the filtration rate being too slow to wash the precipitate. The slurry of precipitate and wash water was extracted with three portions (1 L) of CHCl$_3$, which were dried (MgSO$_4$) and concentrated in vacuo to obtain 4'-methyl-5'-phthalimidomethylpsoralen (9.35 g, 85%). A fourth CHCl$_3$ extract (200 mL) yielded more product (0.663 g) after drying (MgSO$_4$) and evaporation in vacuo. The total yield was 10.013 g (91%), mp 261.5°–265.8° C., of material suitable for use in the next step. An analytical sample, mp 270°–270.5° C., was prepared by recrystallization from glacial acetic acid.

Anal. Calcd. for C$_{21}$H$_{13}$O$_5$N: C, 70.19: H, 3.65; N, 3.90. Found: C, 69.88; H, 3,86; N, 3.73.

5'-aminomethyl-4'-methylpsoralen (E-120).

A mixture of 4'-methyl-5'-phthalimidomethylpsoralen (6.0 g; 16.7 mmol), absolute ethanol (1.2 L, not dried), glacial acetic acid (15.24 mL, 266 mmol), and 85% hydrazine hydrate (7.63 mL, 133 mmol) was heated under reflux for six hours and concentrated in vacuo to an off-white solid. HCl (1 F, 500 mL) was added, followed by NaHCO$_3$(s) until the pH was ca. 8.0, and the mixture was extracted with three portions (500 mL) of CHCl$_3$, which were dried (Na$_2$SO$_4$), and concentrated in vacuo to obtain 5'-aminomethyl-4'-methylpsoralen (E-120) (2.945 g, 77%), mp 153.1°–156.3° C. Recrystallization from a benzene-ligroin (bp 94°–105°) solvent pair gave an analytical sample (73% recovery), mp 154.1°–156.1° C. NMR (CDCl$_3$) δ1.7 (br, s, 2, NH$_2$, exchangeable with D$_2$O), 2.25 (s, 3, 4'-CH$_3$), 3.95 (s, 2, CH$_2$), 6.31 (d, 1, J=9 Hz, C$_3$H), 7.32 (s, 1, C$_8$H), 7.46 (s, 1, C$_5$H), 7.75 (d, 1, J=9 Hz, C$_4$H).

Anal. Calcd. for C$_{13}$H$_{11}$O$_3$N: C, 68.11; H, 4.84; N, 6.11. Found: C, 67.94; H, 4.85; N, 5.82.

5'-AMINOETHYL-4'-ETHYLPSORALEN.

In the same manner as given in the foregoing, but using ethylchloromethyl ketone and chloroethyl methyl ether in Steps 1 and 3, respectively, in place of chloroacetone and chloromethyl methyl ether, the title compound is produced.

5'-AMINOMETHYL-4'-PROPYLPSORALEN.

In the same manner as given in the foregoing, but using propylchloromethyl ketone in Step 1 instead of chloroacetone, the title compound is produced.

In the same manner as given in the foregoing, other variations in selection of starting materials are productive of still other 5'-aminoloweralkyl-4'-loweralkylpsoralens within the scope of the invention in which one or both of the loweralkyl groups present in the compound are varied. As used herein, the term "loweralkyl" comprehends such straight or branched radicals or groups having one to eight carbon atoms, preferably one to four carbon atoms, inclusive, such as methyl, ethyl, propyl, isopropyl, butyl, and the like.

When isolating compounds of the invention in the form of an acid addition salt, the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethanesulphonates, lactates, citrates, tartartes or bitartrates, and maleates. Other acids are likewise suitable and may be employed if desired. For example, fumaric, benzoic, ascorbic, succinic, salicylic, bismethylenesalicylic, propionic, gluconic, malic, malonic, mandelic, cinnamic, citraconic, stearic, palmitic, itaconic, glycolic, benzenesulphonic, and sulphamic acids may also be employed as acid addition salt-forming acids.

PHARMACOLOGY

The biophotosensitization activity of the compounds of the invention is minimal in the erythemal response test according to the procedure of Pathak and Fitzpatrick, J. Invest. Dermatol. 32, 509–518 (1959), entitled "Bioassay of Natural and Synthetic Furocoumarins (Psoralens)", and usually employed standard modifications thereof. As "biophotosensitization activity" is employed herein, however, as well as "photochemical sensitivity on the skin of a mammal", and "photosensitizing" or "photosensitization", as well as "photochemotherapy", the compounds of the invention are active biophotosensitizing agents inasmuch as they produce solely or at best a preponderance of monoaddition or monofunctional addition in the standard tests for DNA photoreactivity, said monofunctional addition being opposed to interstrand cross-linking, as explained in the foregoing. The compounds are thus clearly useful in the further study of reactions and secondary structures of nucleic acids and as inhibitors of RNA replication, and are indicated for employment in the inactivation of viruses as well as in the photochemotherapy of psoriasis and/or tanning by the PUVA procedure, in which they are found to be equally as effective as numerous previously-employed psoralen compounds, without the production of excessive erythema, if any, which is of course dependent upon numerous factors, such as amount of irradiation employed, dosage of the photosensitizing agent, mode of employment (whether topical or oral), and individual skin sensitivities of the mammal subjected to the PUVA therapy, including of course human beings, with respect to which psoriasis is a unique malady. The compounds are accordingly useful for all of the foregoing purposes, but particularly for effecting photochemical sensitivity on the skin of a mammal, these terms as employed herein not being restricted to the production of erythema thereon. They are effective both orally and topically, and the method of effecting photochemical-sensitivity on the skin of a mammal merely comprises the step of orally or topically administering to the said mammal an effective photosensitizing dose of a compound of the invention. When the subject is then exposed to ultraviolet radiation, more particularly ultraviolet "A", in the non-burning range, monofunctional adducts are formed, tanning occurs, and psoriasis is mitigated in human patients, as aforesaid. Other uses of the compounds of the present invention are also set forth in the foregoing.

ERYTHEMA

The erythematic activity of the compounds of the present invention was determined by visual grading of erythemal response according to a modification of the procedure of Pathak and Fitzpatrick, J. Invest. Dermatol. 32, 509–518 (1959), entitled "Bioassay of Natural and Synthetic Furocoumarins (Psoralens)". (The psoralens are of course "linear" isomers of the furocoumarin family.) According to this bioassay, erythema production on albino guinea pig skin is measured visually and the response accorded a gradation definition according to a 0, $\mp$, 1, 2, 3, and 4 scale. The modification employed involved variation of the time between administration of the test compound and exposure to ultraviolet light, thereby enabling measurement of times of onset and decline of the induced erythematic photosensitivity effect.

PROTOCOLS—ERYTHEMA

Each drug is tested orally by administering a dosage of forty (40) mgm/kgm of body weight to groups of fifteen female Hartley albino guinea pigs. The appropriate dosage for each animal is packed into a gelatin capsule and placed far back in the animal's pharynx. Swallowing is assisted by syringe delivery of one to three milliliters of water. The animals are not allowed to eat or drink six hours before and after administration of each product. The exposure of ultraviolet "A" radiation is for two (2) minutes at a dose of 1.14 joules per square centimeter at different times after administration, e.g., 10, 20, 30, 45, 60, 90, 120, 180, 240 minutes after administration. Readings and evaluations are carried out 48 hours post ingestion. Irradiations were made on depiliated regions of the mid-dorsal area of the back in discrete areas (0.5 cm$^2$) using adhesive tape templates. The rest of the animal was covered in black paper.

Gradation: Responses are graded as follows:

0 No response, $\pm$ faint erythema; 1+ erythema; 2+ erythema and slight edema; 3+ erythema and intense edema; and 4+ vesiculobullous reaction.

RESULTS—ERYTHEMA

The compounds of the invention show no oral erythematic activity as read at 48 hours. The compound 5'-aminomethyl-4'-methylpsoralen (E-120), made from 7-hydroxycoumarin as in the foregoing, shows no such erythematic photosensitizing response orally at any post-ingestion time, as read at 48 hours after ingestion for UVA applications at ten (10) through 240 minutes after ingestion, and a low order of oral toxicity at the dosage level tested. In contrast, the control methoxsalen (8-methoxypsoralen), at the same dose level, exhibits a 48-hour after ingestion erythema reading as follows, with the UVA application being at 10, 20, 30, 45, 60, 90, 120, 180 and 240 minutes after ingestion: 0, 0, 1+, 3+, 3+, 3+, 4+, 3+, 2+. The compound E-120 is therefore essentially inactive erythemically.

RESULTS—DNA BINDING

However, in the standard DNA-binding test (references given herein under "Prior Art"), identical amounts of the compound E-120 and 8-methoxypsoralen (8-MOP) exhibited substantially equivalent DNA-binding activity as follows:

E-120  0.83 ± 0.4
8-MOP  1 (arbitrarily assigned as standard)

PROTOCOLS—DNA BINDING TEST

Results—Erythema vs. DNA-monoaddition

According to this DNA unwinding test, stock solutions of the test compounds are prepared and dissolved in absolute ethanol. These stock solutions are used to determined specific absorption coefficients in terms of absorption per microgram of the test compound. Ethanol volumes are kept as low as possible to eliminate the possibility of alteration of the DNA structure. Concentrations of the concentrated, sometimes "saturated", stock solutions are determined by dilution into water and using the specific absorption coefficients determined on the standardized solutions prepared as first-above set forth. All of the absorption spectra are taken in de-ionized water with an ethanol concentration of four percent (4%) or less.

Each sample is then irradiated at a minimum of four (4) ratios of drug to DNA with two (2) irradiation times at each ratio. The irradiation intensity is 1.5 mW/cm$^2$ using black light bulbs (F 20 T 12 BLB-GE). Weight ratios of test compound to DNA are varied over three (3) orders of magnitude for each test compound, and the irradiation times are two (2) hours and twenty (20) hours. Irradiations are performed at 4° C.

Agarose gel electrophoresis is employed to analytically separate linear DNA molecules on a basis of molecular weight, lower molecular weight fragments migrating faster on the gel. Agarose can, under appropriate conditions, also resolve molecules of identical molecular weight, but having different conformations. In fact, supercoiled (Form I), nicked-circular (Form II), and linear (Form III) DNA molecules can be resolved, and this capacity for separation or resolving molecules of identical molecular weight but with different conformations is the basis for the psoralen unwinding assay.

The starting DNA sample consists of a mixture of supercoiled (Form I) (fast-running major band) and nicked-circular (Form II) (slower-running, less intense band). Under the conditions employed, full-length linear DNA migrates between supercoiled and nicked-circular DNA. The less intense, slowest-moving bands, are simply dimer and trimer length molecules which repeat the monomer distribution.

Upon photo-reaction with typical psoralen derivatives, according to the foregoing protocol, the DNA helix unwinds proportionately to the extent of photo-reaction. The unwinding of the DNA helix reduces the super-helical density of the DNA, causing the DNA to migrate more slowly on the agarose gel. Thus, any photo-reaction which causes DNA unwinding, DNA nicking, or DNA fragmentation, can be readily detected with the foregoing agarose gel assay.

In the foregoing psoralen DNA unwinding test procedure, the figure 0.83±0.4 determined for the compound E-120 is definitely indicative of monoaddition of monofunctional DNA-binding activity, as opposed to cross-linking activity. In contrast thereto, for example, highly erythemic compounds which cause extremely strong erythemic reactions upon exposure to identical irradiation conditions show a DNA-binding activity in this test as great as 8±4, which is clearly indicative of cross-linking, a conclusion which is also supported by their highly erythemic activity in the usual erythema test, which is fully discussed in the foregoing.

Therefore, according to the DNA-binding test, the compound E-120 exhibits the same order of effectiveness as does the compound 8-methoxypsoralen, a commonly-employed and widely-recognized photosensitizing agent, without however exhibiting the erythema which is concurrent upon the employment thereof.

COMPOSITIONS AND METHOD OF TREATING

The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference may again be made to U.S. Pat. Nos. 4,124,598 and 4,130,568 for representative examples and disclosure concerning the same. The procedure for preparation of such compositions is conventional in the art. For tanning or oral treatment of psoriasis, the active ingredient is generally formulated in tablets or in gelatin capsules. In such case the diluent may, if desired, be eliminated, although it is generally present. For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 10 mg. to about 50 mg. per kg. of body weight, with a dose in the neighborhood of about 20 mg. per kg. generally being preferred. Such administration and selection of dosage and unit dosage will of course have to be determined according to established medical principles and under the supervision of the physician in charge of the PUVA therapy involved. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carriers of the type already mentioned.

It is to be understood that the invention is not to be limited to the exact details of operation or exact compounds, compositions, methods, or procedures shown and described, as obvious modifications and equivalents will be apparent to one skilled in the art.

I claim:

1. 5'-primaryaminoloweralkyl-4'-loweralkylpsoralen.
2. A compound of claim 1 which is 5'-aminomethyl-4'-methylpsoralen.
3. The method of effecting photochemical sensitivity on the skin of a mammal comprising the step of orally or topically administering to the said mammal an effective photosensitizing dose of a compound of claim 1.
4. The method of claim 3 wherein the compound is 5'-aminomethyl-4'-methylpsoralen.
5. A pharmaceutical composition suitable for use in effecting photochemical sensitivity on the skin of a mammal comprising an effective amount of a compound of claim 1 and a pharmaceutically-acceptable carrier or diluent.
6. The composition of claim 5 wherein the compound is 5'-aminomethyl-4'-methylpsoralen.

* * * * *

UNITED STATES PATENT AND TRADEMARK OFFICE
CERTIFICATE OF CORRECTION

PATENT NO. : 4,370,344

DATED : January 25, 1983

INVENTOR(S) : Kurt D. Kaufman

It is certified that error appears in the above-identified patent and that said Letters Patent is hereby corrected as shown below:

Col. 1, line 27; "emissions" should read -- remissions --
Col. 1, line 30; "past related" should read -- past been related --
Col. 6, line 29; "tartartes" should read -- tartrates --
Col. 7, line 46; "of" should read -- to --
Col. 9, line 7; "of" (second occurrence) should read -- or --

Signed and Sealed this

Seventeenth Day of May 1983

[SEAL]

Attest:

DONALD J. QUIGG

Attesting Officer

Acting Commissioner of Patents and Trademarks